US007015008B2

(12) United States Patent
Shou et al.

(10) Patent No.: US 7,015,008 B2
(45) Date of Patent: Mar. 21, 2006

(54) ANTIBODIES FOR HUMAN CYTOCHROME P450 2D6

(75) Inventors: Magang Shou, Maple Glen, PA (US); Qin Mei, North Wales, PA (US)

(73) Assignee: Merck & Co., Inc., Rahway, NJ (US)

( * ) Notice: Subject to any disclaimer, the term of this patent is extended or adjusted under 35 U.S.C. 154(b) by 0 days.

(21) Appl. No.: 10/381,531

(22) PCT Filed: Sep. 25, 2001

(86) PCT No.: PCT/US01/29884

§ 371 (c)(1),
(2), (4) Date: Mar. 26, 2003

(87) PCT Pub. No.: WO02/26832

PCT Pub. Date: Apr. 4, 2002

(65) Prior Publication Data

US 2004/0023326 A1 Feb. 5, 2004

Related U.S. Application Data

(60) Provisional application No. 60/236,665, filed on Sep. 29, 2000.

(51) Int. Cl.
*C07K 16/40* (2006.01)
*C12N 5/20* (2006.01)
*G01N 33/573* (2006.01)

(52) U.S. Cl. ......................... 435/7.4; 435/18; 435/338; 530/388.26

(58) Field of Classification Search ................. 435/7.4, 435/18, 338; 530/388.26
See application file for complete search history.

(56) References Cited

U.S. PATENT DOCUMENTS

| | | | |
|---|---|---|---|
| 5,693,762 | A | 12/1997 | Queen et al. |
| 5,830,667 | A | 11/1998 | Alvarez et al. |
| 6,054,297 | A | 4/2000 | Carter et al. |
| 6,056,957 | A | 5/2000 | Chou et al. |
| 6,060,253 | A | 5/2000 | Gelboin et al. |
| 6,060,353 | A | 5/2000 | Koh et al. |

FOREIGN PATENT DOCUMENTS

| | | |
|---|---|---|
| WO | WO 95/17516 | 6/1995 |
| WO | WO 00/04861 | 2/2000 |
| WO | WO 00/04864 | 2/2000 |

OTHER PUBLICATIONS

Coon, M. et al. “Cytochrome P450: progress and predictions”, FASEB, 1992, vol. 6, pp. 669-673.
Gelboin, H. et al. “A monoclonal antibody inhibitory to human P450 2D6: a paradigm for use in combinatorial determination of individual P450 role in specific drug tissue metabolism”, Pharmacogenetics, 1997, vol. 7, pp. 469-477.
Gelboin, H. et al. “Inhibitory and Noninhibitory Monoclonal Antibodies to Human Cytochrome P450 2E1”, Chem. Res. Toxicol., 1996, vol. 9, pp. 1023-1030.
Gelboin, H. et al. “Inhibitory and Noninhibitory Monoclonal Antibodies to Human Cytochrome P450 3A3/4”, Biochemical Pharmacology, 1995, vol. 50, pp. 1841-1850.
Gonzalez, F. “The Molecular Biology of Cytochrome P450s”, Pharmacological Reviews, 1989, vol. 40, pp. 243-288.
Guengerich, F. et al. “Cytochrome P-450 Oxidations and the Generation of Biologically Reactive Intermediates”, Advances in Experimental Medicine and Biology, 1991, vol. 283, pp. 1-11.
Guengerich, F. “Metabolic Activation of Carcinogens”, Pharmac. Ther., 1992, vol. 54, pp. 17-61.
Krausz, K. et al. “Inhibitory Monoclonal Antibodies to Human Cytochrome P450 2D6”, Biochemical Pharmacology, 1997, vol. 54, pp. 15-17.
Mei, Q. et al. “Role of a Potent Inhibitory Monoclonal Antibody to Cytochrome P-450 3A4 in Assessment of Human Drug Metabolism”, The Journal of Pharmacology and Experimental Therapeutics, 1999, vol. 291, pp. 749-759.
Nelson, D. et al. “P450 superfamily: update on new sequences, gene mapping, accession numbers and nomenclature”, Pharmacogenetics, 1996, vol. 6, pp. 1-42.
Ngui, J. et al. “Cytochrome P450 3A4-Mediated Interaction of Diclofenac and Quinidine”, Drug Metabolism and Disposition, 2000, vol. 28, pp. 1043-1050.
Shou, M. et al. “Role of human cytochrome P450 3A4 and 3A5 in the metabolism of taxotere and its derivates: enzyme specificity, interindividual distribution and metabolic contribution in human liver”, Pharmacogenetics, 1998, vol. 8, pp. 391-401.
Shou, M. et al. “Role of human hepatic cytochrome P450 1A2 and 3A4 in the metabolic activation of estrone”, Carcinogenesis, 1997, vol. 18, pp. 207-214.
Shou, M. et al. “Sigmoidal kinetic model for two co-operative substrate- binding sites in a cytochrome P450 3A4 active site: an example of the metabolism of diazepam and its derivatives”, Biochem J., 1999, vol. 340, pp. 845-853.
Shou, M. et al. “Use of inhibitory monoclonal antibodies to assess the contribution of cytochromes P450 to human drug metabolism”, European Journal of Pharmacology, 2000, vol. 394, pp. 199-209.
Tang, C. et al. “Major Role of Human Liver Microsomal Cytochrome P450 2C9 (CYP2C9) in the Oxidative Metabolism of Celecoxib, Novel Cyclooxgenase-II Inhibitor”, The Journal of Pharmacology and Experimental Therapeutics, 2000, vol. 293, p. 453-459.

(Continued)

*Primary Examiner*—David Saunders
(74) *Attorney, Agent, or Firm*—Sheldon O. Heber; Jack L. Tribble

(57) ABSTRACT

The present invention features antibodies referred to herein as “MAb50-4” and “MAb184-10”, and polypeptides that compete with MAb50-4 and MAb184-10 for binding to CYP2D6. MAb50-4 can be produced by ATCC No. PTA-3489, while MAb184-10 can be produced by ATCC No. PTA-1999.

16 Claims, 5 Drawing Sheets

OTHER PUBLICATIONS

Tang, C. et al. "Substrate-Dependent Effect of Acetonitrile on Human Liver Microsomal Cytochrome P450 2C9 (CYP2C9) Activity", Drug Metabolism and Disposition, 2000, vol. 28, pp. 567-572.

Yang, T. et al. "Inhibitory Monoclonal Antibody to Human Cytochrome P450 2B6", Biochemical Pharmacology, 1998, vol. 55, pp. 1633-1640.

Shou, M. et al. "Two Inhibitory Monoclonal Antibodies Against Human CYP2D6", Drug Metabolism Reviews, 2000, vol. 32, p 211, abstract No. 149.

Gelboin, H. et al. "Inhibitory monoclonal antibodies to human cytochrome P450 enzymes: a new avenue for drug discovery", Trends in Pharmacological Sciences, 1999, vol. 20, pp. 432-438.

Klein, R. et al. "Overlapping but distinct specificities of anti-liver-kidney microsome antibodies in autoimmune hepatitis type II and hepatitis C revealed by recombinant native CYP2D6 and novel peptide epitopes", Clinical and Experimental Immunology, 1999, vol. 118, pp. 290-297.

Engel, G. et al. "Prediction of CYP2D6-mediated polymorphic drug metablolism (sparteine type) based on in virto investigations", Journal of Chromatography, 1996, vol. 678, pp. 93-103.

ANTIBODIES FOR HUMAN CYTOCHROME P450 2D6

CROSS-REFERENCE TO RELATED APPLICATIONS

The present application is a 371 of International application PCT/US01/29884, filed Sep. 29, 2001, which claims priority to provisional application U.S. Ser. No. 60/236,665, filed Sep. 29, 2000, hereby incorporated by reference herein.

BACKGROUND OF THE INVENTION

The references cited herein are not admitted to be prior art to the claimed invention.

Cytochrome P-450 enzymes are an important enzyme system responsible for the metabolism of drugs, environmental chemicals, and endobiotics. Human cytochrome P-450 enzymes are present in multiple forms that are heterogeneously distributed in individuals and tissues. Multiple forms of P-450 enzymes have different substrate and product specificities that sometimes overlap. (Gonzalez *Pharmacol. Rev.* 40:243–288, 1988; Guengerish et al., *Adv. Exp. Med. Biol.* 283:1–11, 1991; Guengerish et al., *Pharmacol. Ther.* 54:17–61, 1992, Coon et al., *FASEB J.* 6:669–673, 1992; and Nelson et al., *Pharmacogenetics* 6:1–42, 1996.)

One type of P450 enzyme is P450 2D6 (also referred to as "CYP2D6"). CYP2D6 is a debrisoquine hydroxylase that functions in the metabolism of numerous drugs, and is polymorphically expressed. (Gelboin et al., *Pharmacogenetics* 7:469–477, 1977.)

Polymorphism of CYP2D6 was first identified in the human population due, in large part, to the role of CYP2D6 in the oxidation of debrisoquine/sparteine. Subsequent studies have shown that 5–10% of the Caucasian and 1% of the Asian populations carry the autosomal recessive trait for a poor metabolizer. (Conzalez, F. J. (1996) The CYP2D Subfamily. In Cytochromes P450: Metabolic and toxicological aspects. C. Ioannides and D. V. Parke (eds), CRC Press, Inc.)

Inhibitory monoclonal antibodies offer a simple and precise method for assessing the quantitative role of the different P450 enzymes in substrate metabolism. Monoclonal antibodies described as inhibiting CYP2D6 are referenced in Gelboin et al., *Pharmacogenetics* 7:469–477, 1997, Krausz et al., *Biochemical Pharmacology* 54:15–17, 1997, and U.S. Pat. No. 6,060,253.

SUMMARY OF THE INVENTION

The present invention features antibodies referred to herein as "MAb50-4" and "MAb184-10", and polypeptides that compete with MAb50-4 and MAb184-10 for binding to CYP2D6. MAb50-4 can be produced by ATCC No. PTA-3489, while MAb184-10 can be produced by ATCC No. PTA-1999.

Thus, a first aspect of the present invention describes a substantially or partially pure polypeptide preparation comprising a polypeptide that is MAb50-4, MAb 184-10, or that competes with either MAb50-4 or MAb184-10 for binding to human CYP2D6. Reference to "polypeptide" includes single chain polypeptides, and multi-chain polypeptides such as immunoglobulins. Preferred polypeptides competing with MAb50-4 or MAb184-10 for binding to human CYP2D6 are antibodies.

Reference to "substantially or partially pure polypeptide preparation" indicates a polypeptide that makes up at least 10% of the total protein present. In preferred embodiments, the polypeptide represents at least about 50%, at least about 75%, or at least about 95% of the total protein in a sample or preparation. Reference to "substantially or partially pure polypeptide preparation" does not require any purification and may include, for example, chemically synthesized polypeptide that has not been purified.

A polypeptide that competes with either MAb50-4 or MAb184-10 for binding to human CYP2D6 reduces MAb50-4 or MAb184-10 binding by at least about 20%, preferably at least about 50%, when excess and equal amounts of the competing polypeptide and MAb50-4 or MAb184-10 are employed. Binding competition assays can be performed using conditions under which MAb50-4 or MAb184-10 bind to human CYP2D6.

Another aspect of the present invention describes a monoclonal antibody that is either MAb50-4 or MAb184-10 or is a monoclonal antibody that competes with either MAb50-4 or MAb184-10 for binding to human CYP2D6. A "monoclonal" antibody is a homogeneous antibody population. The monoclonal antibody can be produced using different techniques such those involving the use of a hybridoma, or a recombinant cell containing exogenous nucleic acid encoding the antibody.

Another aspect of the present invention describes a monoclonal antibody produced from ATCC No. PTA-3489 (producing MAb50-4) or ATCC No. PTA-1999 (producing antibody MAb184-10). ATCC No. PTA-3489 and ATCC No. PTA-1999 were deposited with the American Type Culture Collection, 10801 University Boulevard, Manassas, Va. 20110-2209, in accordance with Budapest Treaty on Jun. 29, 2001 and Jun. 7, 2000; respectively.

Pursuant to 37 C.F.R. § 1.806 applicants agree that access to the deposits will be available during pendency of the patent application to one determined by the Commissioner to be entitled thereto under 37 CFR § 1.14 and 35 U.S.C. § 122; and, except as permitted under 37 CFR § 1.808(b), all restrictions on the availability to the public of the deposited biological material will be irrevocably removed upon the granting of the patent. Pursuant to 37 C.F.R. § 1.806 applicants agree that the deposits shall be for a term of at least thirty years and at least five years after the most recent request for the furnishing of a sample of the deposit was received by the depository. Pursuant to 37 C.F.R. § 1.805 applicants agree that after being notified that the depository possessing the deposit cannot furnish samples, applicants shall provide a replacement sample and, the failure to provide a replacement sample will cause the application or patent to be treated as if no deposit was made.

Another aspect of the present invention describes a cell line producing a polypeptide that is MAb50-4, MAb184-10, or that competes with either MAb50-4 or MAb184-10 for binding to human CYP2D6. Preferred cells lines are hybridomas, and recombinant cells lines containing recombinant nucleic acid encoding the polypeptide.

Another aspect of the present invention describes a method of assaying for CYP2D6 in a sample. The method comprises the steps of: (a) contacting the sample with a polypeptide, preferably an antibody, described herein; and (b) measuring the ability of the polypeptide to bind to material present in the sample.

Another aspect of the present invention describes a method of determining whether CYP2D6 metabolizes a compound. The method comprises the steps of: (a) combining CYP2D6, the compound, and a polypeptide described herein that specifically inhibits CYP2D6 catalyzed metabolism of bufuralol by at least about 75%, preferably, the polypeptide is either MAb50-4, MAb184-10, or a monoclonal antibody that competes with either MAb50-4 or MAb184-10 for binding to human CYP2D6; and (b) measuring the ability of CYP2D6 to metabolize the compound.

Other features and advantages of the present invention are apparent from the additional descriptions provided herein including the different examples. The provided examples illustrate different components and methodology useful in practicing the present invention. The examples do not limit the claimed invention. Based on the present disclosure the skilled artisan can identify and employ other components and methodology useful for practicing the present invention.

DETAILED DESCRIPTION OF THE INVENTION

Figure 1:
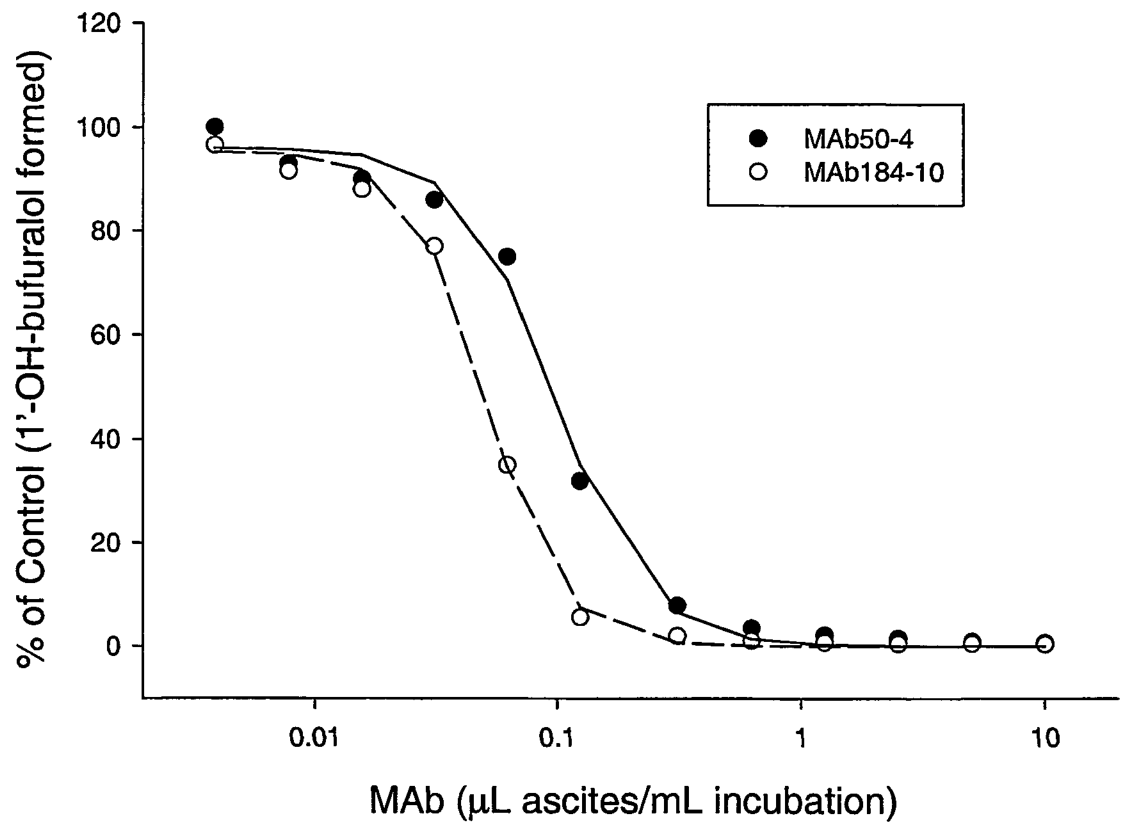
FIG. 1 illustrates MAb50-4 and MAb184-10 inhibition of bufuralol 1'-hydroxylation by CYP2D6. Monoclonal antibody ascites and CYP2D6 (15 pmol) in 970 $\mu$l of 0.1 M phosphate buffer were preincubated at room temperature for 5 minutes. The reaction was initiated with the addition of 25 $\mu$M bufuralol and 1 mM NADPH in 1 mL and incubated at 37° C. for 10 minutes. The percentage of the control was determined on High Performance Liquid Chromatograph (HPLC) by comparing 1'-OH-bufuralol formed to the internal standard in the presence and absence of monoclonal antibody. Data are the mean of duplicate determinations.

Monoclonal antibodies MAb50-4 and MAb184-10 bind to human CYP2D6 and selectively inhibit CYP2D6 activity. The CYP2D6 regions bound by MAb50-4 and MAb184-10 provide target sites for polypeptide binding and, preferably, for selectively inhibiting CYP2D6 activity.

Polypeptide binding to CYP2D6 has a variety of different uses, such as in determining whether CYP2D6 may be present in a sample. Preferred polypeptides selectively bind CYP2D6.

Selectively binding to CYP2D6 is determined with respect to at least the following non-target P450 enzymes: CYP1A1 CYP1A2, CYP2A6, CYP2B6, CYP2C8, CYP2C9, CYP2C19, CYP2E1, CYP3A4, CYP3A5 and CYP3A7. A polypeptide selectively binding CYP2D6 has one or both of the following characteristics: (1) the polypeptide binds to CYP2D6 at least about 10-fold, more preferably at least 100-fold, stronger than it binds to one or more, preferably, all the non-target P450 enzymes; and (2) the polypeptide detectable binds to CYP2D6 under conditions where it does not detectable bind to one or more, preferably all, non-target P450 enzymes. The ability of a polypeptide to bind to a P450 non-target enzyme and to CYP2D6 can be measured using conditions such as those described in the Examples provided below.

More preferred polypeptides are those that selectively inhibit CYP2D6 activity. Polypeptides selectively inhibiting CYP2D6 activity can be used to provide information on the interaction and contribution of individual P450s to the metabolism of drugs and drug candidates. Such information may useful for predicting drug efficacy, drug interaction and drug toxicity.

Selectively inhibiting CYP2D6 activity is determined with respect to at least the following non-target P450 enzymes: CYP1A1, CYP1A2, CYP2A6, CYP2B6, CYP2C8, CYP2C9, CYP2C19, CYP2E1, CYP3A4, CYP3A5 and CYP3A7. A polypeptide selectively inhibits CYP2D6 if it significantly inhibits bufuralol metabolism while inhibiting one or more, preferably all, P450 non-target enzymes less than about 25%, preferably less than about 10%, and more preferably, less than about 5%. Significant inhibition of bufuralol metabolism is achieved by inhibiting bufuralol by at least about 50%, preferably, at least 75%, and more preferably at least about 90%. The percentage of inhibition can be measured using different conditions, such as those described in the Examples provided below.

Polypeptides able to bind to CYP2D6 include antibodies, antibody fragments, and derivatives thereof. The basic structural unit of an antibody contains four polypeptide chains that provide for a Fc region joined to two Fab regions through a hinge region. (See, for example, Breitling et al., Recombinant Antibodies, John Wiley & Sons, Inc. and Spektrum Akademischer Verlag, 1999; and Lewin, Genes IV, Oxford University Press and Cell Press, 1990.)

In naturally occurring antibodies the four polypeptide chains contain two identical heavy chains and two identical light chains. Heavy and light chains each contain a constant region and a variable region. Within the variable regions are hypervariable regions responsible for antigen specificity.

The carboxy region of the two heavy chain polypeptides are constant regions joined by disulfide binding to produce an Fc region. The Fc region is important for providing biological activity such as complement and macrophage activation. Each of the two heavy chain polypeptides making up the Fc region extend into different Fab regions through a hinge region.

Fab regions each contain a light chain made up of a variable region and a constant region, and a heavy chain region containing a variable region and a constant region. A light chain is joined to a heavy chain by disulfide bonding through constant regions.

The light and heavy chain variable regions of a Fab region provide for an Fv region that participates in antigen binding.

Specificity of the Fv region is determined by three hypervariable regions (also referred to as complementarity determining regions), that are interposed between more conserved flanking regions (also referred to as framework regions). Amino acids associated with framework regions and complementarity determining regions can be numbered and aligned as described by Kabat et al., Sequences of Proteins of Immunological Interest, U.S. Department of Health and Human Services, 1991.

In higher vertebrates there are two classes of light chains and five classes of heavy chains. The light chains are either κ or λ. The heavy chains define the antibody class and are either α, δ, ε, γ, or μ. For example, IgG has a γ heavy chain. Subclasses also exist for different types of heavy chains such as $\gamma_1$, $\gamma_2$, $\gamma_3$, and $\gamma_4$. Heavy chains impart a distinctive conformation to hinge and tail region. (Lewin, Genes IV, Oxford University Press and Cell Press, 1990.)

Subclasses can be further characterized. For example, $IgG_2$ subtypes can be further divided into $IgG_{2a}$ and $IgG_{2b}$. (Hahn G. S. (1982) Antibody Structure, Function and Active Sites. In *Physiology of Immunoglobulins: Diagnostic and Clinical Aspects.* S. E. Ritzmann (ed) Alan Liss Inc., New York; and Turner M. W. (1983) Immunoglobulins. In *Immunology in Medicine. A Comprehensive Guide to Clinical Immunoglobulins.* 2nd Edition. E. J. Holborow & W. G. Reeves (eds.) Grune & Stratton, London.)

Polypeptides Competing with Either MAb50-4 or MAb184-10

Polypeptides competing with either MAb50-4 or MAb184-10 for binding to human CYP2D6 can be obtained using different techniques. Suitable techniques include selecting for a competing antibody using a competition assay involving MAb50-4 or MAb184-10, deriving a polypeptide comprising a Fv fragment from either MAb50-4 or MAb184-10, and deriving a polypeptide comprising a Fv fragment from an antibody identified as competing with either MAb50-4, or MAb184-10.

Based on the information provided in a Fv fragment a large number of different polypeptide derivatives that bind to an antigen can be produced. Preferred derivatives contain modifications made to constant or variable regions of an MAb50-4 or MAb184-10, or a fragment thereof, to obtain a polypeptide that still binds to the antibody target. Examples of different types of modifications include the addition, deletion, substitution, and alteration, of one or more amino acids. The ability of a particular polypeptide to compete with MAb50-4 or MAb184-10 can be determined using competition studies.

Suitable polypeptides can be derived from antibodies by making modifications to different antibody regions. The modifications can be made to different regions such as the Fc region or an Fab constant region. If the Fab constant region is removed, the variable region heavy and light regions making up Fv can be joined by a polypeptide linker.

Suitable polypeptide can also be derived by making modifications within a Fv region, particularly the framework region. The ability to produce such modifications is illustrated in different references concerning humanization of antibodies. (See, for example, U.S. Pat. Nos. 5,693,762, 6,054,297, and 6,056,957.)

Preferred polypeptides are monoclonal antibodies. Monoclonal antibodies are precise, stable, and highly specific reagents that can quantitatively measure the amount of individual P450s. They are generally of greater specificity than either polyclonal antibodies or chemical inhibitors. In addition, since monoclonal antibodies can exhibit a strong non-competitive inhibition kinetics, the contribution of a P450 to the metabolism of a specific drug can be determined precisely regardless of [S], $K_m$ and type of substrate and catalytic reaction. Thus, a monoclonal antibody specifically binding and/or inhibitory to a single P450 can be used to identify and quantify the role of that P450 in the metabolism of a substrate in a tissue containing a multiplicity of P450 forms. The extent of inhibition affected by the monoclonal is a measure of the contribution of the target P450 to the metabolic reaction.

Polypeptide Production

Polypeptides can be produced using standard techniques including those involving chemical synthesis, recombinant nucleic acid techniques, and the use of a hybridoma. Techniques for chemical synthesis of polypeptides are well known in the art. (See e.g., Vincent, in *Peptide and Protein Drug Delivery,* New York, N.Y., Dekker, 1990.)

Recombinant nucleic acid techniques employ a nucleic acid template for polypeptide synthesis. Examples of techniques for in vitro translation, and introducing nucleic acid into a cell and expressing the nucleic acid to produce protein are well known in the art. (See, Ausubel, *Current Protocols in Molecular Biology,* John Wiley, 1987–1998, and Sambrook et al., in *Molecular Cloning, A Laboratory Manual,* 2nd Edition, Cold Spring Harbor Laboratory Press, 1989.)

A variety of different cell lines of different origin can be used for recombinant antibody expression, including those from prokaryotic organisms (e.g., *E. coli,* Bacillus, and Streptomyces) and from Eukaryotic (e.g., yeast, Baculovirus, and mammalian). (Breitling et al., Recombinant Antibodies, John Wiley & Sons, Inc. and Spektrum Akademischer Verlag, 1999.) Nucleic acid encoding for an antibody can be introduced into a host using an expression vector that may exist autonomously from the host chromosome. Alternatively, nucleic acid encoding for an antibody may be integrated into the host chromosome. (For example, see, International Application No. WO 95/17516.)

A hybridoma is an immortalized antibody producing cell line. Examples of techniques for producing and using hybridoma are described in the Examples provided below, and in references such as Ausubel *Current Protocols in Molecular Biology,* John Wiley, 1987–1998, Harlow et al., *Antibodies, A Laboratory Manual,* Cold Spring Harbor Laboratory, 1988, and Kohler et al., *Nature* 256, 495–497, 1975.

Determining CYP2D6 Expression Levels

Polypeptides specifically binding to CYP2D6 can be employed to determine the expression level of CYP2D6. Different types of formats for using polypeptides to detect the level of an enzyme are well known in the art.

In general, an assay determining CYP2D6 expression levels involves contacting a sample with a polypeptide specific for CYP2D6 and measuring polypeptide binding to material present in the sample. Polypeptide binding can be measured using different techniques such as those employing a polypeptide containing a detectable label and those using an antibody recognizing a CYP2D6 specific polypeptide. Detectable labels include fluorescent labels, radioactive labels, and enzymes wherein a substrate is metabolized to a quantifiable product (e.g., wherein the enzyme is alkaline phosphatase and the substrate is 5-bromo-4-chloro-3-indolyl-phosphate/nitroblue tetrazolium).

In an embodiment of the present invention CYP2D6 expression is determined by using the following steps: components of a sample are separated on a gel such as an SDS polyacrylamide gel, transferred to a piece of material capable of adsorbing the separated sample (e.g., nitrocellulose paper), contacted with a first antibody specific for CYP2D6, and contacted with a second antibody specific for the first antibody and which comprises a detectable label. The amount of CYP2D6 is then quantitated by assaying for the detectable label.

Determining CYP2D6 Activity and Compound Metabolism

CYP2D6 activity and the degree of compound metabolism can be measured by assaying for bufuralol metabolism using techniques well known in the art. One way by which the degree of metabolism could be measured is by measuring the substrate and product levels after stopping a reaction and comparing the activity level with a control sample where an inhibitory polypeptide was not added. For example, the reaction could be stopped by the adding dichloromethane, the metabolites then extracted from the aqueous phase to the organic phase, the organic phase dried out, and the residue of the sample applied to a TPLC immediately for separation and quantitation of metabolites. Other methods for determining the level of metabolism are also acceptable and included herein.

In an embodiment of the present invention, CYP2D6 activity on a substrate is measured in a method that comprises (1) contacting a sample containing the substrate with an antibody that specifically inhibits CYP2D6 activity; (2) measuring substrate and product levels; and (3) comparing the substrate and product levels with levels obtained from a control sample containing CYP2D6 and substrate, but not the antibody. The degree of variation indicates the contribution of CYP2D6 to the metabolism of the substrate.

EXAMPLES

Examples are provided below to further illustrate different features of the present invention. The examples also illustrate useful methodology for practicing the invention. These examples do not limit the claimed invention.

Example 1

Experimental Procedures

Different experimental protocols that were employed for obtaining and characterizing antibodies are provided below.

Preparation of Human P450s

Human cDNAs for P450s 3A4, 3A7, 1A1, 1A2, 2A6, 2B6, 2C8, 2C9, 2C19, 2D6 and 2E1 and OR (P450 oxidoreductase) were individually inserted into baculovirus expression vectors. *Spondoptera frugipedra* (Sf21) insect cells were infected separately with the recombinant viruses to express the P450 proteins. Supersome CYP3A5+OR was purchased from Gentest Inc. Microsomes from Sf21 cells expressing the individual P450s were prepared and stored at −80° C. until used. P450 content and protein concentration were determined. For metabolism studies, P450 proteins were co-expressed with OR and their specific activities measured with marker substrates (Table 1).

TABLE 1

Specific assays for twelve individual P450s

| P450 | Substrate | Product |
|---|---|---|
| 3A4 | Testosterone | 6β-OH-testosterone |
| 3A5 | Testoterone | 6β-OH-testosterone |
| 3A7 | Testosterone | 6β-OH-testosterone |
| 1A1 | Phenanthrene | 9,10-dihydrodiol |
| 1A2 | Phenacetin | Acetaminophen |
| 2A6 | Coumarin | 7-OH-coumarin |
| 2B6 | Diazepam | Nordiazepam |
| 2C8 | Taxol | 6α-OH-taxol |
| 2C9 | Flurbiprofen | 4'-OH-flurbiprofen |
| 2C19 | Mephenytoin | 4'-OH-mephenytoin |
| 2D6 | Bufuralol | 1'-OH-bufuralol |
| 2E1 | Chlorzoxazone | 6-OH-chlorzoxazone |

$IC_{50}$ Determination of Monoclonal Antibodies $IC_{50}$ values were calculated using the Grafit version 3.09 (Data Analysis and Graphic Program, Erithancus Software Ltd., Staines, UK) as follows:

$$v = \frac{V_o}{1 + \left(\frac{I}{IC_{50}}\right)^s}$$

where $V_o$ is an uninhibited velocity, v is an observed velocity, s is a slope factor, and I is an inhibitor concentration.

Immunization of Mice and Hybridoma Production

Three female Balb/c mice were immunized by i.p. injection three times for 4–6 weeks with 50 μg of Sf21 cell microsomes containing baculovirus-expressed CYP2D6 protein emulsified in 0.2 mL of complete Freund's adjuvant (first immunization), followed by two immunizations with incomplete Freund's adjuvant. Three days after the third injection, one mouse was killed and the spleen removed. The fusion of myeloma cells with primed, dissociated spleen cells was carried out by treatment with PEG 5000. Cells diluted with HAT medium were dispensed into ten 96-well tissue culture plates at a density of 10,000 cells/well (0.2 mL/well). Hybridomas were picked and grown in selective HAT medium.

Screening for the Production of Antibodies

Monoclonal antibody screening was performed by ELISA using alkaline phosphatase-conjugated goat $F(ab')_2$ fragment to mouse IgG(H+L) and mouse IgG (Fc specific). Immunoassay plates were coated either with Sf21 microsomes containing baculovirus-expressed CYP2D6 at 1 pmol/well (100 μL) or wild type baculovirus infected Sf21 cell microsomes using 1×coating solution. As the hybridomas began to grow, the spent medium from each well was screened for the presence of antibodies to CYP2D6 by ELISA. Each positive well was rescreened and then subcloned using complete medium with 10% FBS. Hybridomas of interest were resubcloned at least two to three times to guarantee they were monoclonal.

Immunoblot Analysis

Expressed P450s from Sf21 cells and liver microsomal proteins (1 pmol/well) were subjected to SDS-PAGE, transferred onto nitrocellulose and probed with monoclonal antibodies from culture fluid or ascites. Monoclonal antibodies binding was detected using alkaline phosphatase conjugated goat anti-mouse antibodies.

Antibody Characterization

Isotyping was carried out using the Ouchterlony immunodiffusion technique provided by the mouse monoclonal antibody typing kits (The Binding Site, Inc.).

Preparation of Ascites Fluid Containing Monoclonal Antibodies

Hybridoma cells were injected into the peritoneal cavity of each mouse at a density of $10^6$ cells/mouse for preparation of ascites fluid after priming with pristane. Ascites fluid containing highly concentrated monoclonal antibodies was recovered from each mouse after 2–3 weeks (3~5 mL/mouse).

Monoclonal Antibody Inhibition of CYP2D6

A typical 1-mL incubation contained monoclonal antibodies (0.0039 to 40 $\mu$L of ascites fluid as needed) and 0.1 M potassium phosphate buffer (pH=7.4) containing 10–30 pmol of CYP2D6 or other P450s or 30 pmol (total P450) as human liver microsomes in 970 $\mu$L. The mixture was preincubated at room temperature for 5 minutes and the reaction was initiated by the addition of NADPH (1 mM) and substrate (dissolved in methanol) in a final volume of 1 mL and incubated for 10–30 minutes at 37° C. Anti-MK-0677 monoclonal antibody was used as a control for non-specific binding. Metabolite was extracted with 8 volumes of dichloromethane after the addition of internal standard for quantitation of metabolite(s) and dried under a stream of nitrogen gas. The residue was dissolved in 100 $\mu$L of 50–80% methanol or acetonitrile in water and immediately analyzed by HPLC or LC-MS. Marker assays for determining the cross-reactivity of the monoclonal antibodies with P450s other than CYP2D6 are listed in Table 1.

Example 2

Results

Results concerning the generation and characterization of antibodies to human CYP2D6 are provided below.

Preparation of Monoclonal Antibodies Specific to Human CYP2D6

Mice were immunized with CYP2D6-enriched microsomes of Sf21 cells infected with recombinant baculoviruses encoding CYP2D6 cDNA. Three weeks after immunization dispersed spleen cells from the immunized mice were fused with myeloma cells resulting in the formation of more than 3,000 hybridoma clones in HAT selective culture. 191 hybridoma clones producing antibodies with positive binding activity to CYP2D6 were identified by ELISA. Of the 191 hybridomas, two clones (defined as MAb184-10 and MAb50-4) produced monoclonal antibodies that strongly inhibited CYP2D6 enzyme activity using in vitro assays (FIG. 1). However, neither of the two monoclonal antibodies yielded immunoblot with CYP2D6 protein, suggesting the epitope(s) on CYP2D6 is/are highly conformational. The isotype of immunoglobulin of the monoclonal antibodies was identified as $IgG_{2b}$ for MAb50-4 and $IgG_{2a}$ for MAb184-10 by the Ouchterlony immunodiffusion technique.

Inhibitory Effect of the Monoclonal Antibodies on CYP2D6

Mouse ascites containing MAb184-10 or MAb50-4 was examined for its inhibitory effect on CYP2D6-catalyzed bufuralol 1'-hydroxylation, which is generally used as an indicator for CYP2D6 activity. FIG. 1 shows the titration curve of inhibition vs. volume of ascites. Addition of 1 $\mu$L of ascites to a 1 mL incubation containing 10–15 pmol of CYP2D6, resulted in the inhibition of the CYP2D6-catalyzed bufuralol metabolism greater than 98%. The $IC_{50}$ values for MAb50-4 and MAb184-10 were determined to be 0.101±0.005 and 0.05±0.002 $\mu$L ascites/mL incubation, respectively, suggesting that the activity of the monoclonal antibodies is extremely high.

Inhibitory Cross-Reactivity of the Monoclonal Antibodies with Other P450s

Figure 2:
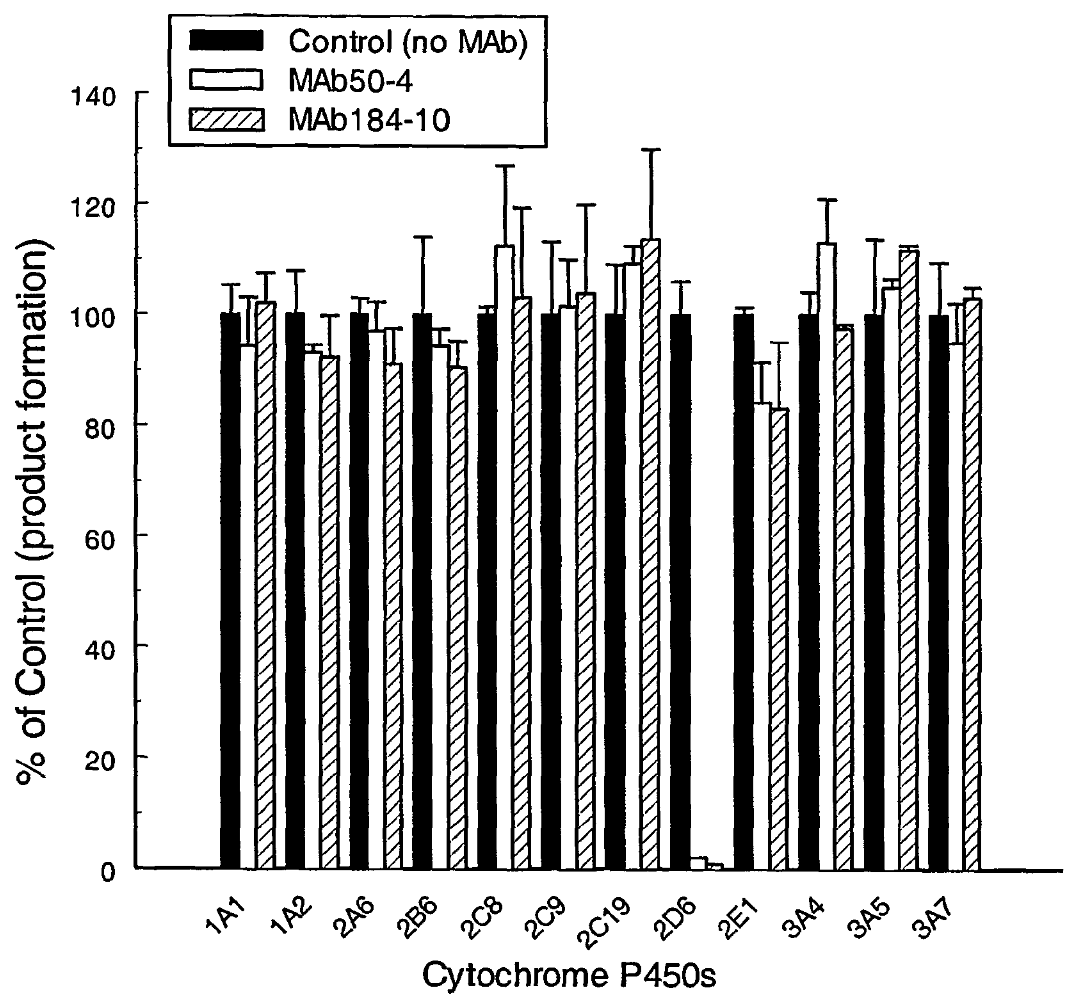
FIG. 2 illustrates specificity of MAb50-4 and MAb184-10 inhibition of the metabolism of marker substrates by twelve recombinant human P450s. Specific assays for individual P450s are shown in Table 1, infra. The MAbs were used as 1 $\mu$l mouse ascites/mL of incubation mixture containing 10–30 pmol of the recombinant P450s. All samples were analyzed by HPLC. Data are the mean of triplicate determinations with a standard error.
Figure 3:
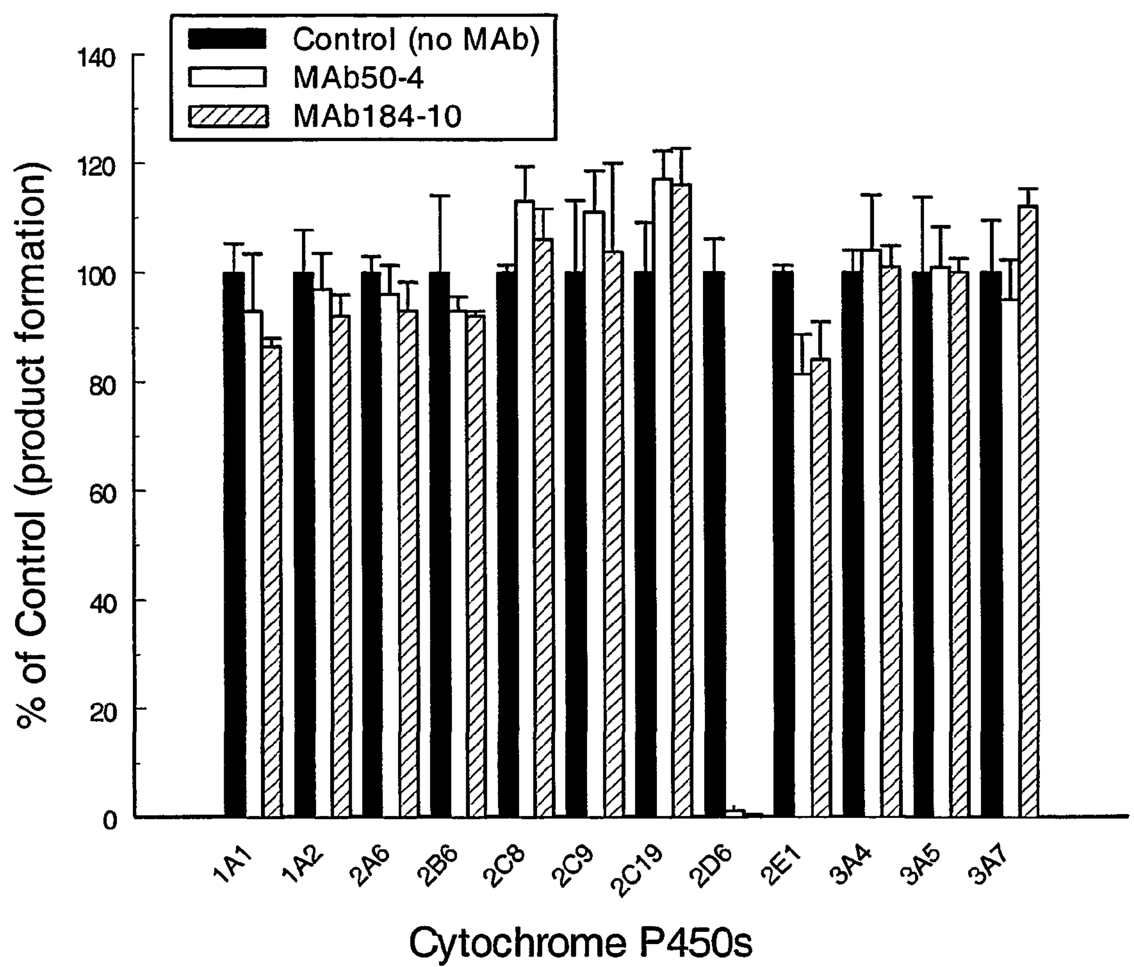
FIG. 3 illustrates specificity of MAb50-4 and MAb184-10 inhibition of the metabolism of marker substrates by twelve recombinant human P450s. Specific assays for individual P450s are shown in Table 1. The MAbs were used as 5 $\mu$l mouse ascites in 1 mL of incubation mixture containing 10–30 pmol of the recombinant P450s. All samples were analyzed by BPLC. Data are the mean of triplicate determinations with a standard error.

To determine the specificity of the monoclonal antibodies, marker assays for eleven other human cDNA-expressed P450s were examined (Table 1). The monoclonal antibodies at 1 $\mu$L of ascites/mL incubation were found to inhibit CYP2D6-catalyzed bufuralol metabolism by 99% but did not display significantly inhibitory cross-reactivity towards any of the other eleven human cDNA-expressed human CYP1A1 (phenanthrene 9-hydroxylation), CYP1A2 (phenacetin O-deethylation), CYP2A6 (coumarin 7-hydroxyalation), CYP2B6 (diazepam N-demethylation), CYP2C8 (taxol 6α-hydroxylation), CYP2C9 (flurbiprofen 4'-hydroxylation), CYP2C19 (mephenytoin 4'-hydroxylation), CYP2E1 (chlorzoxazone 6-hydroxylation), CYP3A4 (testosterone 6β-hydroxylation), CYP3A5 (testosterone 6β-hydroxylation) and CYP3A7 (testosterone 6β-hydroxylation) (FIG. 2). No cross-reaction was observed when the volume of monoclonal antibody ascites was raised to 5 $\mu$L/mL incubation (FIG. 3). Thus, the inhibitory effect of the two monoclonal antibodies is highly specific to CYP2D6.

Contribution of CYP2D6 to Bufuralol Metabolism in Human Liver Microsomes

Figure 4:
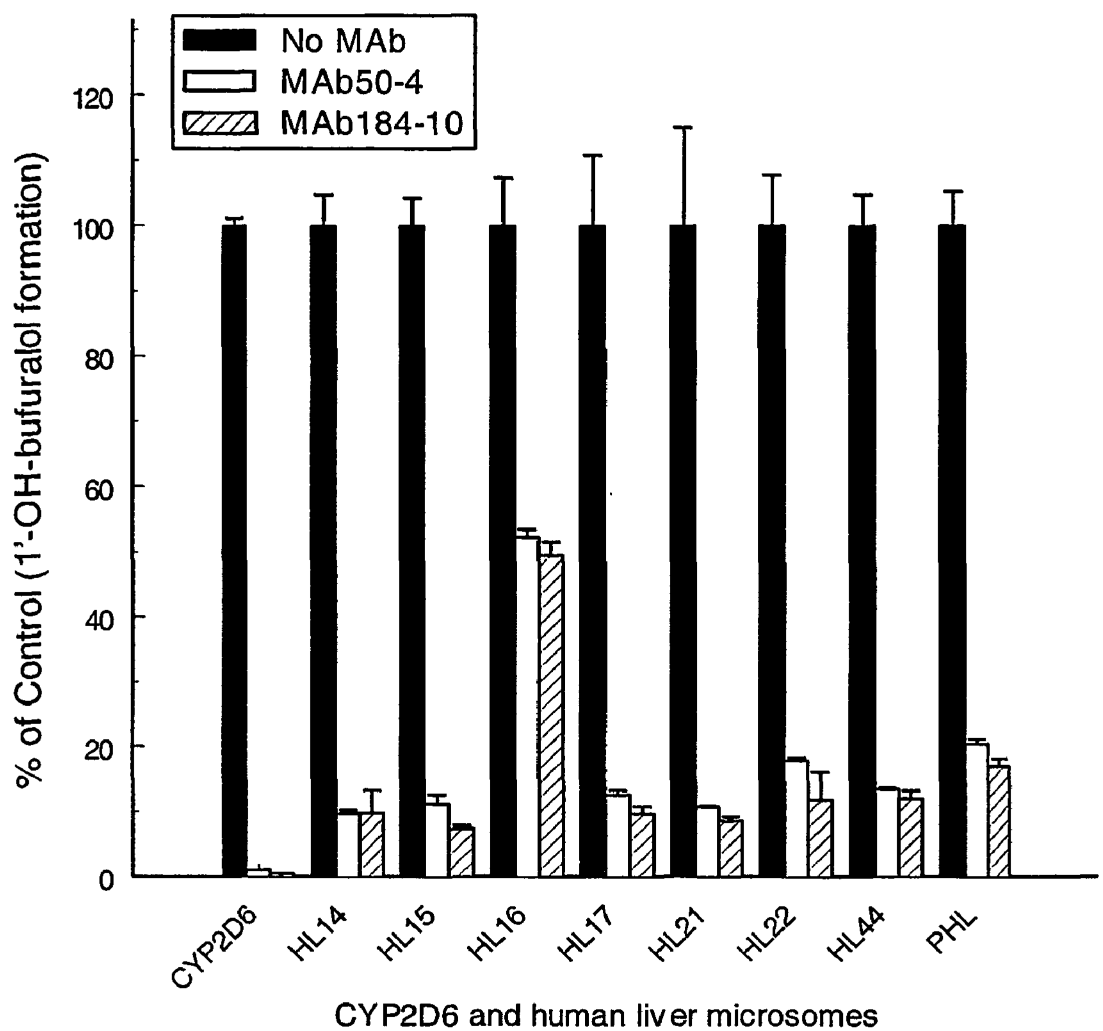
FIG. 4 illustrates an assessment of human CYP2D6 contribution to bufuralol 1'-hydroxylation in a panel of seven human liver microsomes (HL) using MAb50-4 and MAb184-10. MAb (5 $\mu$l ascites fluid) and HL (30 pmol) in 1 mL of incubation mixture containing cofactors were incubated at 37° C. for 10 minutes after 5-minute preincubation. PHL=pooled human liver microsomes. Control specific activities (nmol/min, nmol) of bufuralol 1'-hydroxylase in human liver microsomes were 2.5 (HL14), 1.4 (HL15), 0.8 (HL16), 5.8 (HL17), 3.7 (HL18), 2.5 (HL19) and 1.5 (PHL), respectively.

Inhibitory MAb184-10 and MAb50-4 were used to determine the contribution of CYP2D6 to bufuralol 1'-hydroxylation in human liver preparations. Upon examination of seven individuals, basal activity of the human liver microsomes for bufuralol metabolism varied from 0.9 to 5.9 nmol/min, nmol. With the addition of monoclonal antibodies, CYP2D6-dependent activity was inhibited from a low of 47% to a high of 93%, depending on the liver donors (FIG. 4). These results suggest that other P450s in addition to CYP2D6 play a role in the metabolism of bufuralol. FIG. 4 shows that the inhibitory effect of both MAb50-4 and MAb184-10 in each sample was fairly consistent.

Figure 5:
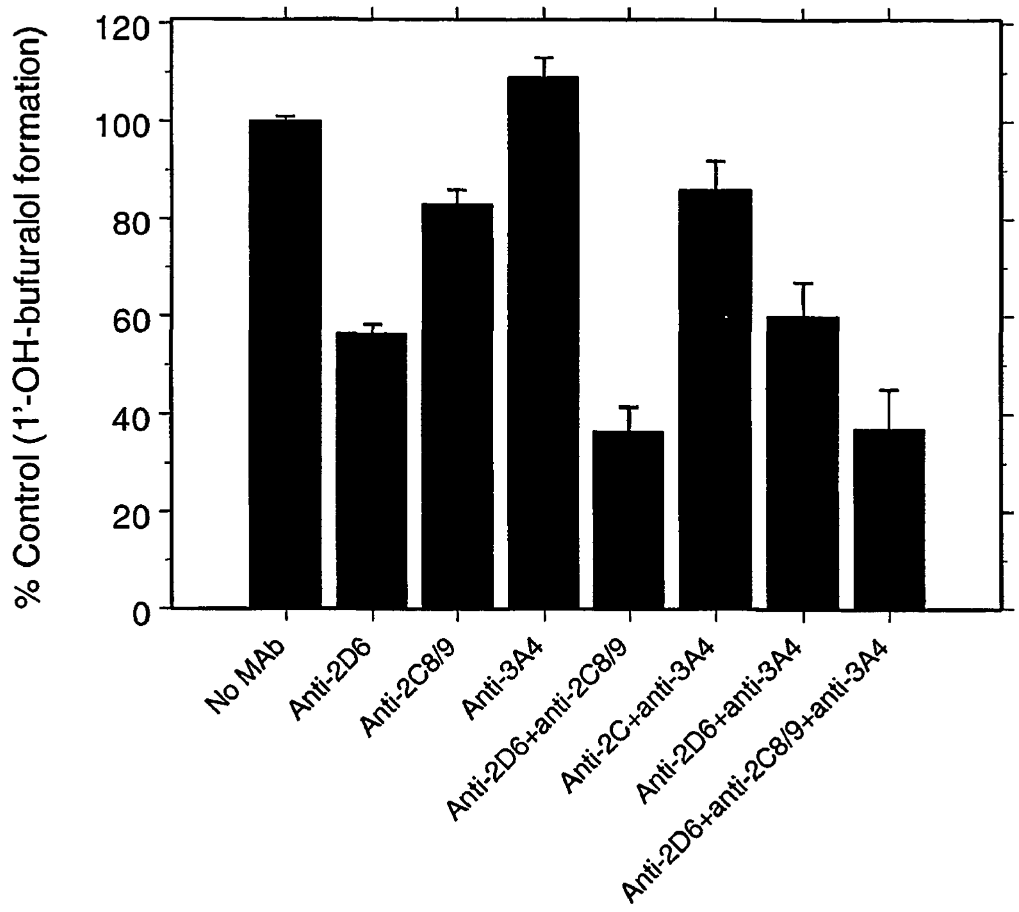
FIG. 5 illustrates an assessment of contribution of single and multiple P450s to bufuralol 1'-hydroxylation in HL16 by the combined use of inhibitiory MAbs specific to CYP2D6, CYP3A4 and CYP2C8/9.

Interestingly, in one of the seven human liver microsomes (HL16), CYP2D6 contributed only 47% of total bufuralol 1'-hydroxylase activity. In order to determine the contribution of other P450s, further analysis of the HL16 was undertaken using the three inhibitory monoclonal antibodies specific for CYP2D6, CYP2C8/9 and CYP3A4 singly or in combination. The quantitative contribution of these P450s singly to bufuralol metabolism in HL16 was determined to be 43% for CYP2D6, 17% for CYP2C8/9 and negligible for CYP3A4 (FIG. 5). When the three monoclonal antibodies were added together to the HL16 microsomes, the additive effects of the inhibitory monoclonal antibodies were observed and the total bufuralol 1'-hydroxylase of the HL16 was inhibited by more than 63%. Thus, CYP2D6 and CYP2C8/9 contributed approximately 44% and 17%, respectively, to the metabolism of bufuralol. The role of other P450s for the remaining enzyme activity (37%) in HL16 remains unclear. These results demonstrate the utility of an inhibitory monoclonal antibody in determining the contribution of an individual P450 to the metabolism of a given drug in human tissue.

Other embodiments are within the following claims. While several embodiments have been shown and described, various modifications may be made without departing from the spirit and scope of the present invention.

What is claimed is:

1. A substantially or partially pure polypeptide preparation comprising a polypeptide that is MAb50-4 or MAb184-10.

2. The polypeptide of claim 1, wherein said polypeptide is MAb50-4.

3. The polypeptide of claim 1, wherein said polypeptide is MAb184-10.

4. A method of assaying for cytochrome P450 2D6 in a sample comprising the steps of:

a) contacting said sample with the polypeptide of claim 1; and b) measuring the ability of said polypeptide to bind to material present in said sample.

5. A monoclonal antibody that is either MAb50-4 or MAb184-10.

6. The monoclonal antibody of claim 5, wherein said antibody is MAb50-4.

7. The monoclonal antibody of claim 5, wherein said antibody is MAb184-10.

8. A method of assaying for cytochrome P450 2D6 in a sample comprising the steps of:

a) contacting said sample with the antibody of claim 5; and b) measuring the ability of said antibody to bind to material present in said sample.

9. A cell line producing a antibody that is either MAb50-4 or MAb184-10.

10. The cell line of claim 9, wherein said antibody is MAb50-4.

11. The cell line of claim 9, wherein said antibody is MAb 184-10.

12. The cell line of claim 9, wherein said cell line is ATCC No. PTA-3489.

13. The cell line of claim 9, wherein said cell line is ATCC No. PTA-1999.

14. A method of determining whether cytochrome P450 2D6 metabolizes a compound comprising the steps of:

a) combining cytochrome P450 2D6, said compound, and a monoclonal antibody that is MAb50-4or MAb184-10; and b) measuring the ability of cytochrome P450 2D6 to metabolize said compound.

15. The method of claim 14, wherein said antibody is MAb50-4.

16. The method of claim 14, wherein said antibody is MAb 184-10.

* * * * *